United States Patent
Wang et al.

(10) Patent No.: US 11,548,848 B2
(45) Date of Patent: Jan. 10, 2023

(54) SYNTHESIS AND APPLICATION OF ALCOHOL AMINE WITH EXPENDED MAIN CARBON CHAIN

(71) Applicant: Beijing University of Technology, Beijing (CN)

(72) Inventors: Jianfeng Wang, Beijing (CN); Yan Song, Beijing (CN); Mingzhang Lan, Beijing (CN); Suping Cui, Beijing (CN); Yan Wang, Xingtai (CN); Lei Chang, Xinjiang county (CN); Yali Wang, Beijing (CN); Xiaoyu Ma, Beijing (CN)

(73) Assignee: BEIJING UNIVERSITY OF TECHNOLOGY, Beijing (CN)

( * ) Notice: Subject to any disclaimer, the term of this patent is extended or adjusted under 35 U.S.C. 154(b) by 0 days.

(21) Appl. No.: 17/401,599

(22) Filed: Aug. 13, 2021

(65) Prior Publication Data

US 2022/0234992 A1 Jul. 28, 2022

(30) Foreign Application Priority Data

Jan. 28, 2021 (CN) .......................... 202110122228.8

(51) Int. Cl.
| | | |
|---|---|---|
| *C07C 213/08* | (2006.01) | |
| *B01J 27/02* | (2006.01) | |
| *B01J 31/02* | (2006.01) | |
| *C04B 24/12* | (2006.01) | |
| *C07C 213/10* | (2006.01) | |
| *C07C 215/08* | (2006.01) | |
| *C04B 103/52* | (2006.01) | |

(52) U.S. Cl.
CPC ............. *C07C 213/08* (2013.01); *B01J 27/02* (2013.01); *B01J 31/0232* (2013.01); *C04B 24/122* (2013.01); *C07C 213/10* (2013.01); *C07C 215/08* (2013.01); *C04B 2103/52* (2013.01)

(58) Field of Classification Search
None
See application file for complete search history.

(56) References Cited

PUBLICATIONS

Townsend et al. (Tetrahedron (1991), 47(14-15), 2591-602) (Year: 1991).*

* cited by examiner

*Primary Examiner* — Sudhakar Katakam
*Assistant Examiner* — Jennifer C Sawyer
(74) *Attorney, Agent, or Firm* — WPAT, PC

(57) ABSTRACT

Synthesis and application of an alcohol amine with an extended main carbon chain are provided, belonging to the field of chemical building materials. Under the action of a catalyst, tertiary amine is subjected to a two-step substitution reaction, a hydrolytic reaction and a reducing reaction to obtain a novel alcohol amine (NAA). The novel alcohol amine as provided may have a better grinding aid effect than triethanolamine while is added into cement as a cement grinding aid, and thus has a wide application prospect.

8 Claims, 1 Drawing Sheet

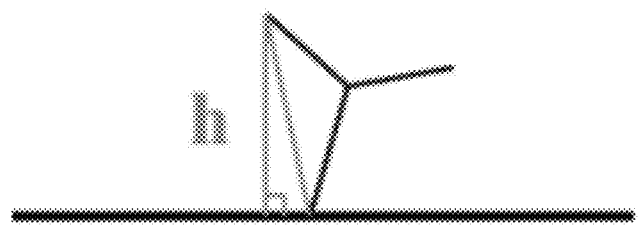
Sole Figure

SYNTHESIS AND APPLICATION OF ALCOHOL AMINE WITH EXPENDED MAIN CARBON CHAIN

TECHNICAL FIELD

The invention relates to a synthesis method and an application of a novel alcohol amine, which belongs to the field of chemical building materials, and is mainly used in the direction of cement admixtures, especially in the field of cement grinding aid production.

BACKGROUND OF THE INVENTION

Cement grinding is one of the most important links in a cement production process, and power consumption in a grinding process accounts for about 60% to 70% of total energy consumption of cement production, of which grinding power consumption of cement products accounts for 30%-40% of the total power consumption. The grinding process of cement is a process in which particles of cement materials (such as clinker, admixture, gypsum, etc.) change from large to small, is also an energy conversion process in which electrical energy is converted into mechanical energy and then into surface energy of cement powder, and energy conversion efficiency directly determines a utilization rate of energy. At present, ball mills are mostly used to grind cement with a low energy conversion rate which is generally below 15% mainly due to the fact that the cement particles produce agglomeration effect during a ball milling process. By adding a small number of grinding aids in the cement grinding process, the tendency of fine particles to agglomerate can be alleviated and the energy utilization rate of the ball mill is increased. Data show that output of cement can be obviously improved by adding the grinding aids with an effective substance content of 0.01% to 0.03% into the ball mill, and therefore, the cement grinding aid is a green and environmentally friendly product that saves energy, reduces consumption, and improves output and quality.

At present, main components of commercial grinding aids are alcohol organics, alcohol amine organics and some inorganic salts. A grinding aid prepared with such small molecular substances has some drawbacks when used: grinding aid ability has an upper limit, generally 10%-15%; adaptability of ground cement and concrete admixture is not good, which affects mixing amount; and the grinding aid is high in salt content, which is harmful to the production of high-quality durable cement. But the fundamental/root cause for limited development of grinding aids at present is that the main components of grinding aids are tertiary amines (such as triethanolamine, triisopropanolamine, diethanol monoisopropanolamine, ethanol diisopropanolamine).

It is generally believed that surface active molecules in the grinding aids form a monomolecular adsorption film on surfaces of material particles, which reduces agglomeration among the particles and stickiness among the particles, a grinding medium and a liner, thereby improving the grinding efficiency. Therefore, a film-forming thickness and film-forming efficiency of grinding aid molecules have a direct influence on a grinding aid effect of the grinding aids. In addition, existing tertiary amines are mainly prepared by reacting ammonia gas with ethylene oxide or propylene oxide, so that only alcohol amine with ethanol-based or isopropanol-based molecular structures can be obtained, and an alcohol group with three or more carbon atoms on a main chain cannot be obtained. Based on this concept, the invention synthesizes a novel alcohol amine substance based on the molecular structure design, and promotes further improvement of the performance of the grinding aids.

SUMMARY OF THE INVENTION

An objective of the invention is to break through the bottleneck of output improving capacity of the current grinding aids. Therefore, a method for synthesizing an alcohol amine with an extended main carbon chain and its application in cement grinding aids are disclosed.

The invention provides a method for synthesizing a novel alcohol amine (NAA), including the following steps: adding a triethanolamine (R—OH) and a catalyst of concentrated sulfuric acid into a reaction vessel to mix uniformly, and then slowly adding hydrobromic acid and heating to 80° C.-110° C., where a molar ratio of the hydrobromic acid to the triethanolamine is 1:1; cooling and distilling to obtain bromoethanolamine after reacting for 30-60 minutes, adding a cyanating agent and the catalyst into the distilled solution, reacting for 50-80 minutes at a temperature of 110° C.-240° C. to obtain cyanoethanolamine, then adding an 70%-80% (by weight) sulfuric acid aqueous solution, heating and hydrolyzing to obtain carboxylolamine, and finally adding a reducing agent of lithium aluminum tetrahydrogen and refluxing, reducing to obtain the novel alcohol amine (NAA) with an extended main carbon chain. Reaction formulas are as follows:

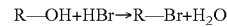

R—OH+HBr→R—Br+H₂O

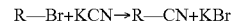

R—Br+KCN→R—CN+KBr

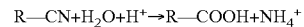

R—CN+H₂O+H⁺→R—COOH+NH₄⁺

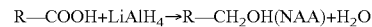

R—COOH+LiAlH₄→R—CH₂OH(NAA)+H₂O

A novel alcohol amine, which is characterized in that a hydroxyl group in the triethanolamine is substituted with a halogen atom and a cyanide ion in two steps, and then hydrolyzed to generate carboxylic acid, and finally an alcohol amine compound with an extended main carbon chain is obtained through lithium aluminum tetrahydrogen reduction reaction, that is, the —OH in the original structure reacts to be —CH2-OH.

Preferably, the reaction step is two-step substitution of halogen atoms and cyanide ions, followed by hydrolysis and reduction to form an extended carbon chain.

Preferably, the triethanolamine is one or more of triethanolamine, diethanol monoisopropanolamine, ethanol diisopropanolamine and triisopropanolamine.

More preferably, the triethanolamine is triisopropanolamine.

Preferably, the cyanating agent is one or two of potassium cyanide, sodium cyanide, zinc cyanide and potassium ferrocyanide.

Preferably, the catalyst is one of N-methylpyrrolidone and dimethylformamide.

Preferably, a bromine atom substitution reaction temperature ranges from 85° C. to 105° C.

Preferably, a cyanide ion substitution reaction temperature ranges from 150° C. to 200° C., and the reaction time lasts for 60-80 minutes.

Preferably, the reducing agent is lithium tetrahydroaluminum.

The invention also provides an application of a novel alcohol amine in cement grinding aids, where an aqueous solution with 8%-50% of a novel alcohol amine cement grinding aid is added into cement, and a mixing amount of the alcohol amine cement grinding aid is 0.02%-0.15% of the cement mass. Preferably, the mixing amount of the cement grinding aid is 0.03%-0.1% of the cement by mass.

The novel alcohol amine prepared in the invention may have the technical advantages that: the molecular structure of the novel alcohol amine has one more methylene group than the original tertiary amine, and the carbon chain structure is extended. After an adsorption reaction of the hydroxyl group and the cement particles, the novel alcohol amine molecules form a larger annular space layer and a larger molecular layer thickness under the influence of hydrogen bonds, thereby producing a stable film with a thicker molecular layer, and opening gaps among cement particles wider and achieving a better grinding aid effect. The materials studio calculation software is used to simulate molecular layer thicknesses of different novel alcohol amines, and the results showed that the molecular layer of the novel alcohol amine prepared by the invention was thicker than the original tertiary amine before the reaction.

BRIEF DESCRIPTION OF THE FIGURE

The FIGURE is a schematic diagram showing adsorption of alcohol amine molecules on surfaces of cement minerals.

DETAILED DESCRIPTION OF PREFERRED EMBODIMENTS

The invention is further illustrated in detail in combination with the embodiments hereinafter, but to which the invention is not limited.

Embodiment 1

14.9 grams (g) of triethanolamine is added into a flask, 3 milliliters (ml) of concentrated sulfuric acid is slowly added while the flask is shaken to uniformly mix the triethanolamine with the concentrated sulfuric acid, and 22.5 g of 36% (by weight) hydrobromic acid is added into a dropping funnel; then, a reaction bottle is heated to 100° C., and cooled for distillation 50 minutes after the reaction; 5 ml of N-methylpyrrolidone is added and heated to 160° C., a potassium ferrocyanide solution is slowly added, cooled and distilled 60 minutes after the reaction; and finally, 5 ml of a 80% (by weight) sulfuric acid aqueous solution is added, heated and refluxed, and lithium tetrahydroaluminum is added, and distillation is performed after the reaction is ended to obtain a novel alcohol amine with an extended main carbon chain.

Embodiment 2

19.1 g of triisopropanolamine is added into a flask, 3 ml of concentrated sulfuric acid is slowly added while the flask is shaken to uniformly mix the triisopropanolamine with the concentrated sulfuric acid, and 22.5 g of 36% (by weight) hydrobromic acid is added into a dropping funnel; then, a reaction bottle is heated to 100° C., and cooled for distillation 50 minutes after the reaction; 5 ml of N-methylpyrrolidone is added and heated to 150° C., a potassium ferrocyanide solution is slowly added, and cooled and distilled 60 minutes after the reaction; and finally, 5 ml of a 80% (by weight) sulfuric acid aqueous solution is added, heated and refluxed, and lithium tetrahydroaluminum is added, and distillation is performed after reaction is ended to obtain a novel alcohol amine with an extended main carbon chain.

Embodiment 3

16.3 g of diethanol monoisopropanolamine is added into a flask, 3 ml of concentrated sulfuric acid is slowly added while the flask is shaken to uniformly mix the diethanol monoisopropanolamine with the concentrated sulfuric acid, and 22.5 g of 36% hydrobromic acid is added into a dropping funnel; then, a reaction bottle was heated to 105° C., and cooled for distillation 50 minutes after the reaction; 5 ml of N-methylpyrrolidone is added and heated to 170° C., a potassium ferrocyanide solution is slowly added, and cooled and distilled 60 minutes after the reaction; and finally, 5 ml of a 80% (by weight) sulfuric acid aqueous solution is added, heated and refluxed, and lithium tetrahydroaluminum then is added, and distillation is performed after the reaction is ended to obtain a novel alcohol amine with an extended main carbon chain.

Embodiment 4

17.7 g of ethanol diisopropanolamine is added into a flask, 3 ml of concentrated sulfuric acid is slowly added while the flask is shaken to uniformly mix the ethanol diisopropanolamine with the concentrated sulfuric acid, and 22.5 g of 36% hydrobromic acid is added into a dropping funnel; then, a reaction bottle is heated to 105° C., and cooled for distillation 50 minutes after the reaction; 5 ml of N-methylpyrrolidone is added and heated to 170° C., a potassium ferrocyanide solution is slowly added, and cooled and distilled 60 minutes after the reaction; and finally, 5 ml of a 80% sulfuric acid aqueous solution is added, heated and refluxed, and lithium tetrahydroaluminum then is added, and distillation is performed after the reaction is ended to obtain a novel alcohol amine with an extended main carbon chain.

Embodiment 5

Molecular layer thicknesses of the novel alcohol amine molecules obtained in Embodiments 1-4 on the surfaces of cement minerals are calculated by simulation (in a Material studio calculation software Dmol3 module) (Table 1). Adsorption of the alcohol amine molecules on the surfaces of cement minerals is shown in the FIGURE, and a distance from the most distal ends of the molecules to the surface is selected as a molecular layer thickness. The molecular layer thicknesses of the alcohol amine molecules adsorbed on the surfaces of the cement minerals before and after the reaction are compared, the novel alcohol amines obtained in the four embodiments can increase the thickness of the surface molecular layer compared with the original tertiary amine

TABLE 1

Simulation results of thickness of the molecular layer formed by alcohol amine on cement surface before and after reaction

| Serial number | Molecular layer thickness (angstroms) | |
| --- | --- | --- |
| | Before reaction | After reaction |
| Embodiment 1: | 7.719 | 7.918 |
| Embodiment 2: | 7.803 | 8.015 |
| Embodiment 3: | 7.786 | 7.967 |
| Embodiment 4: | 7.811 | 8.022 |

Embodiment 6: (Application Embodiment)

The novel alcohol amine with the extended main carbon chain obtained in Embodiments 1-4 is diluted with water to obtain a cement grinding aid sample with a concentration of 40% (by weight). Portland cement clinker is crushed with a jaw crusher, and the crushed materials are screened and processed to control the materials to be about 1-6 mm 3 kg of test materials, of which 2850 g is clinker and 150 g is gypsum are weighed, 1.5 g of the cement grinding aid sample prepared in Embodiments 1-4 is added, ground in a SYMΦ500×500 mm standard cement test mill for 25 min, where discharge time lasted for 5 min. The discharged cement passes through a 0.6 mm standard sieve to remove the large particles that have not been ground, and then is dried and stored in a sealed bag to test fineness and particle size distribution of the sieve residues. A chemical composition and a mineral composition of clinker are shown in Table 2, where gypsum is natural dihydrate gypsum, in which the content of crystal water is 18% and the content of $SO_3$ is 42%.

A negative-pressure sieve analyzer is used to test cement sieve residues, and a laser particle size distribution analyzer is used to test the particle distribution of cement by a dry method. Before the test, the cement sample needs to be dried at 105° C. for 2 hours to remove water. During the test, 30 g of the cement sample is weighed, a shading ratio is kept at 10%-20%, and the number of tests is set to 15 times. The test results are shown in Table 3 and Table 4. It could be seen from Table 3 and Table 4 that compared with the original tertiary amine before the reaction, the four novel alcohol amines with extended main carbon chains could reduce the 45 μm sieve residues and increase distribution of 3-32 μm particles. The sieve residues and 3-32 μm particle content are important indicators of the grinding aid effect of cement grinding aid. The smaller the 45 μm sieve residues and the higher 3-32 μm particle content, the better the surface cement grinding aid effect.

TABLE 2

Chemical composition and mineral composition of clinker (%)

| Loss | $SiO_2$ | $Al_2O_3$ | $Fe_2O_3$ | CaO | MgO |
|---|---|---|---|---|---|
| 0.41 | 21.39 | 5.66 | 5.34 | 63.22 | 2.10 |

| f-CaO | $SO_3$ | $C_3S$ | $C_2S$ | $C_3A$ | $C_4AF$ |
|---|---|---|---|---|---|
| 0.60 | 0.33 | 47.63 | 25.42 | 5.94 | 16.23 |

TABLE 3

45 μm sieve residues of cement particles (%)

| | 45 μm sieve residues (%) | |
|---|---|---|
| Serial number | Before reaction | After reaction |
| Control group | | 20.7 |
| Embodiment 1: | 17.7 | 16.9 |
| Embodiment 2: | 17.0 | 16.2 |
| Embodiment 3: | 17.6 | 16.9 |
| Embodiment 4: | 17.5 | 16.7 |

TABLE 4

Influence of polyalcohol amines on cement particle size distribution (%)

| Before reaction | Control group | Triethanolamine | Triisopropanolamine | Diethanol monoisopropanolamine | Ethanol diisopropanolamine |
|---|---|---|---|---|---|
| 0-3 μm | 7.86 | 7.34 | 7.58 | 7.37 | 7.41 |
| 3-32 μm | 54.37 | 58.92 | 59.13 | 58.97 | 59.05 |
| 32-45 μm | 5.04 | 6.02 | 6.03 | 5.92 | 5.97 |
| >45 μm | 32.73 | 27.72 | 27.26 | 27.74 | 27.57 |

| After reaction | Control group | Embodiment 1: | Embodiment 2: | Embodiment 3: | Embodiment 4: |
|---|---|---|---|---|---|
| 0-3 μm | 7.86 | 7.41 | 7.65 | 7.46 | 7.52 |
| 3-32 μm | 54.37 | 60.34 | 60.75 | 60.67 | 60.62 |
| 32-45 μm | 5.04 | 6.12 | 6.08 | 5.96 | 6.14 |
| >45 μm | 32.73 | 26.13 | 25.52 | 25.91 | 25.72 |

What is claimed is:

1. A method for synthesizing a novel alcohol amine (NAA) with an extended main carbon chain, comprising the following steps:

adding a tertiary amine (R—OH) and a catalyst of concentrated sulfuric acid into a reaction vessel to mix uniformly, then adding hydrobromic acid and heating to 80° C.-110° C. for reacting, cooling and distilling to obtain bromoethanolamine after the reacting for 30-60 minutes, wherein a molar ratio of hydrobromic acid to tertiary amine is 1:1;

adding a cyanating agent and the catalyst into the distilled solution, and reacting for 50-80 minutes at a temperature of 110° C.-240° C. to obtain cyanoethanolamine;

after obtaining the cyanoethanolamine, adding an 70%-80% sulfuric acid aqueous solution, heating and hydrolyzing to obtain carboxylolamine; and adding a reducing agent and refluxing, reducing the carboxylolamine to obtain an alcohol amine with an extended main carbon chain;

the reaction scheme for synthesizing the novel alcohol amine (NAA) with an extended main carbon chain is as follows:

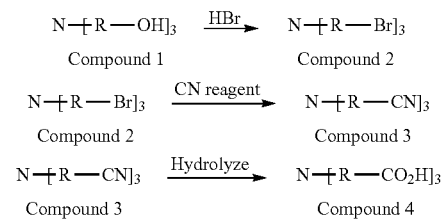

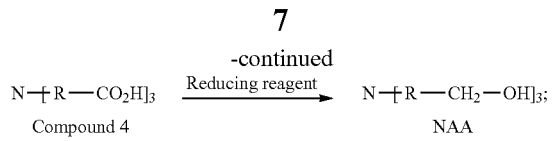

in the reaction scheme, the compound 1 is the tertiary amine (R—OH), the compound 2 is the bromoethanolamine, the compound 3 is the cyanoethanolamine, the compound 4 is the carboxylolamine and the NAA is the novel alcohol amine (NAA) with an extended main carbon chain.

2. The method for synthesizing a novel alcohol amine (NAA) with an extended main carbon chain according to claim 1, wherein a hydroxyl group in the tertiary amine is substituted with a bromine atom and a cyanide ion in two steps, and then hydrolyzed to generate carboxylic acid, and finally an alcohol amine compound with the extended main carbon chain is obtained through a lithium aluminum tetrahydrogen reduction reaction, that is, the —OH in an original structure reacts to be —CH$_2$—OH.

3. The method for synthesizing a novel alcohol amine (NAA) with an extended main carbon chain according to claim 1, wherein the tertiary amine is one or more selected from the group consisting of triethanolamine, diethanol monoisopropanolamine, ethanol diisopropanolamine and triisopropanolamine.

4. The method for synthesizing a novel alcohol amine (NAA) with an extended main carbon chain according to claim 1, wherein the cyanating agent is one or two selected from the group consisting of potassium cyanide, sodium cyanide, zinc cyanide and potassium ferrocyanide.

5. The method for synthesizing a novel alcohol amine (NAA) with an extended main carbon chain according to claim 1, wherein the catalyst is one of N-methylpyrrolidone and dimethylformamide.

6. The method for synthesizing a novel alcohol amine (NAA) with an extended main carbon chain according to claim 1, wherein a temperature of bromine atom substitution reaction ranges from 85° C. to 105° C.

7. The method for synthesizing a novel alcohol amine (NAA) with an extended main carbon chain according to claim 1, wherein a temperature of cyanide ion substitution reaction ranges from 150° C. to 200° C., and a time of the cyanide ion substitution reaction lasts for 60-80 minutes.

8. The method for synthesizing a novel alcohol amine (NAA) with an extended main carbon chain according to claim 1, wherein the reducing agent is lithium tetrahydroaluminum.

* * * * *